US011077136B2

(12) United States Patent
Escaich Ferrer et al.

(10) Patent No.: US 11,077,136 B2
(45) Date of Patent: Aug. 3, 2021

(54) COMPOSITIONS FOR THE SKIN

(71) Applicant: BIOIBERICA, S.A.U., Palafolls (ES)

(72) Inventors: José Escaich Ferrer, Palafolls (ES); Sergi Segarra López, Sabadell (ES); Javier Córdoba Lucio, Vic (ES); Jorge Flores García, Parets del Vallès (ES); Alfonso Velasco Franco, Premià de Dalt (ES)

(73) Assignee: BIOIBERICA, S.A.U., Palafolls (ES)

( * ) Notice: Subject to any disclaimer, the term of this patent is extended or adjusted under 35 U.S.C. 154(b) by 49 days.

(21) Appl. No.: 16/094,300

(22) PCT Filed: Apr. 12, 2017

(86) PCT No.: PCT/EP2017/058877
§ 371 (c)(1),
(2) Date: Oct. 17, 2018

(87) PCT Pub. No.: WO2017/182379
PCT Pub. Date: Oct. 26, 2017

(65) Prior Publication Data
US 2019/0192553 A1    Jun. 27, 2019

(30) Foreign Application Priority Data
Apr. 18, 2016 (ES) ............................... ES201630479

(51) Int. Cl.
| | |
|---|---|
| *A61K 31/728* | (2006.01) |
| *A61K 31/52* | (2006.01) |
| *A61K 31/01* | (2006.01) |
| *A61K 31/726* | (2006.01) |
| *A23L 33/115* | (2016.01) |
| *A61P 17/06* | (2006.01) |
| *A61P 17/02* | (2006.01) |
| *A61K 9/48* | (2006.01) |
| *A61K 31/202* | (2006.01) |
| *A61K 31/737* | (2006.01) |

(52) U.S. Cl.
CPC .......... *A61K 31/728* (2013.01); *A23L 33/115* (2016.08); *A61K 9/4825* (2013.01); *A61K 31/01* (2013.01); *A61K 31/202* (2013.01); *A61K 31/52* (2013.01); *A61K 31/726* (2013.01); *A61K 31/737* (2013.01); *A61P 17/02* (2018.01); *A61P 17/06* (2018.01); *A23V 2002/00* (2013.01); *A23V 2200/318* (2013.01); *A23V 2250/1872* (2013.01); *A23V 2250/1874* (2013.01); *A23V 2250/1882* (2013.01); *A23V 2250/51* (2013.01)

(58) Field of Classification Search
CPC .... A61K 31/01; A61K 31/726; A61K 31/728; A61K 31/202; A61K 9/4825; A61K 31/737; A61K 31/53; A61P 17/02; A61P 17/06; A23L 33/115; A61V 2250/1872; A61V 2250/51; A61V 2250/1882; A61V 2250/1874; A61V 2200/318; A61V 2002/00

See application file for complete search history.

(56) References Cited

U.S. PATENT DOCUMENTS

| | | | |
|---|---|---|---|
| 4,780,414 A | 10/1988 | Nimrod et al. | |
| 4,784,990 A * | 11/1988 | Nimrod | A61P 27/02 514/54 |
| 7,204,859 B2 | 4/2007 | Cottard et al. | |
| 7,226,584 B2 | 6/2007 | Lersch et al. | |
| 7,722,682 B2 * | 5/2010 | Cottard | A61K 8/29 8/405 |
| 7,763,594 B2 | 7/2010 | Escaich et al. | |
| 7,947,303 B2 * | 5/2011 | Kessler | A23L 33/175 424/439 |
| 8,540,782 B2 | 11/2013 | Hashimoto et al. | |
| 8,933,255 B2 * | 1/2015 | Miller | A61P 1/04 554/111 |
| 8,937,194 B2 * | 1/2015 | Miller | A61K 8/361 554/111 |
| 9,006,339 B2 | 4/2015 | Fleischhaker et al. | |
| 2004/0097404 A1 | 5/2004 | Kessler et al. | |
| 2011/0256247 A1 | 10/2011 | Miller | |
| 2014/0302171 A1 | 10/2014 | Takahashi et al. | |

FOREIGN PATENT DOCUMENTS

| | | |
|---|---|---|
| EP | 0 238 994 A2 | 9/1987 |
| EP | 1 064 946 A2 | 1/2001 |
| EP | 1 634 599 A1 | 3/2006 |
| WO | 2007/059874 A2 | 5/2007 |
| WO | 2015/040067 A1 | 3/2015 |

OTHER PUBLICATIONS

Berroth et al., "Role of Fibroblasts in the Pathogenesis of Atopic Dermatitis," Journal of Allergy and Clinical Dermatology, 131, 1547-1554 (Jun. 2013); Exhibit A supplied by applicant.*
Ahmad et al., "Evaluation of Wound Closure Activity of Cocos Nucifera Oil on Scratched Monolayer of Human Dermal Fibroblasts," Chemical Engineering Transactions, 56, 1657-1662 (2017; Exhibit B supplied by applicant.*
Park et al., "The Novel Cytokine p43 Stimulated Dermal Fibroblast Proliferation and Wound Repair," American Journal of Pathology, 166(2), 387-398 (Feb. 2005; Exhibit C supplied by applicant.*
Morhenn et al., "The Rate of Wound Healing Is Increased in Psoriasis," Journal of Dermatol Sci, 72(2), 87-92 (Nov. 2013; Exhibit D supplied by applicant.*

(Continued)

*Primary Examiner* — Lawrence E Crane
(74) *Attorney, Agent, or Firm* — Hayes Soloway PC

(57) ABSTRACT

The present invention relates to a composition comprising hyaluronic acid, dermatan sulfate, at least one omega-3 fatty acid, and at least one nucleotide. It also relates to the new composition for use in the treatment or prevention of diseases, ailments, dysfunctions, or alterations of the skin, preferably atopic dermatitis. The composition may be in the form of a pharmaceutical composition, food supplement, functional food, or medical food.

16 Claims, 5 Drawing Sheets

(56) References Cited

OTHER PUBLICATIONS

"Bioiberica: Aquasorb", XP-002769989, Nov. 18, 2015, 2 pages.
"Bioiberica: Bioiberica to launch Aquasorb, a range of products for atopic dermatitis and psoriasis", XP-002769990, Nov. 18, 2015, 3 pages.
Spanish Search Report for 201630479 dated Apr. 18, 2016.
International Search Report for PCT/EP2017/058877 dated Jul. 7, 2017 [PCT/ISA/210].
"Frequently Asked Questions About Medical Foods; Second Edition—Guidance for Industry", 2016, 1-12, U.S. Department of Health and Human Services, Food and Drug Administration, Center for Food Safety and Applied Nutrition.
Andreas Berroth, "Atopic Dermatitis and Skin Disease—Role of Fibroblasts in the Pathogenesis of Atopic Dermatitis", Journal, 2013, 1547-1554.e6, Journal of Allergy and Clinical Immunology, vol. 131, No. 6.
Sang Gyu Park, "Growth Factors, Cytokines, Cell Cycle Molecules—The Novel Cytokine p46 Stimulates Dermal Fibroblast Proliferation and Wound Repair", Journal, 2005, 387-398, American Journal of Pathology, vol. 166, No. 2, American Society for Investigative Pathology.
Vera B_ Morhenn, "The Rate of Wound Healing is Increased in Psoriasis", Manuscript, 2013, 1-12, Journal of Dermatological Science, vol. 72, No. 2, Japanese Society for Investigative Dermatology.
Zunairah Ahmad, "Evaluation of Wound Closure Activity of Cocos Nucifera Oil on Scratched Monolayer of Human Dermal Fibroblasts", Article, 2017, 1657-1662, Chemical Engineering Transactions, vol. 56, The Italian Association of Chemical Engineering.
Giuseppe Stinco, "Pruritus in Chronic Plaque Psoriasis: a Questionnaire-based Study of 230 Italian Patients", Article, 2014, 122-128, vol. 22, No. 2, Acta dermatovenerologica Croatica: ADC.
G. Yosipovitch, "The Prevalence and Clinical Characteristics of Pruritus among Patient with Extensive Psoriasis", Journal, 2000, 969-973, vol. 143, British Journal of Dermatology 2000.

* cited by examiner

O-3 = omega-3 fatty acids
HA = hyaluronic acid
DS = dermatan sulfate
N = nucleotides
ZnO = zinc oxide

COMPOSITIONS FOR THE SKIN

This application is a National Stage of International Application No. PCT/EP2017/058877, filed Apr. 12, 2017, which claims priority from Spanish Patent Application No. P 201630479, filed Apr. 18, 2016.

TECHNICAL FIELD OF THE INVENTION

The present invention relates to a new composition. Likewise, it also relates to the new composition for use in the treatment or prevention of diseases, ailments, dysfunctions, or alterations of the skin, especially atopic dermatitis, and also to restore the integrity of the skin. The composition may be in the form of pharmaceutical composition, food supplement, functional food, or medical food.

BACKGROUND OF THE INVENTION

Atopic dermatitis is a type of chronic inflammatory dermatosis that is characterized by scaly and itchy rashes. It is a multifactorial disease that results from the interaction of genetic factors, defects in the barrier function, environmental factors, susceptibility to skin infections, and a series of immunological factors. It is fundamentally a childhood disease, but may persist into adulthood.

Atopic dermatitis is a disease that is quite frequent in pets. The existence of a racial predisposition in dogs appears to indicate the importance of genetic factors.

Fibroblasts, along with keratinocytes, are the principal cells in the dermis and epidermis. Their migration and proliferation are involved in the process of re-epithelialization, which plays a very necessary role in skin pathologies in which the dermal barrier is altered and patients present lesions caused by the pathology itself or by scratching due to itching. In fact, fibroblasts are known to be involved in the pathogenesis of atopic dermatitis (A. Berroth et al., *J. Allergy Clin. Immunol.* 131(6), 1547-1554 (2013)).

Steroids, antihistamines, or antibiotics are normally prescribed to treat atopic dermatitis. The use of these drugs over an extended period of time may cause several undesirable side effects.

A new composition is therefore required for the effective treatment of atopic dermatitis, without side effects.

Polyunsaturated Fatty Acids (PUFA) are fatty acids that contain more than one double bond between the carbon atoms thereof. They are involved in important metabolic routes in living organisms. They can be obtained from oily fish and vegetables such as walnuts, corn, sunflower seeds, or soybeans. It is important to highlight two series of polyunsaturated fatty acids, the omega-3 series and the omega-6 series. Omega-3 fatty acids have beneficial effects on the risk factors for cardiovascular diseases, such as hypertension, hypertriglyceridemia, and hypercholesterolemia. Some of the more important omega-3 fatty acids include eicosapentaenoic acid (EPA) and docosahexaenoic acid (DHA), and among the omega-6 fatty acids, gamma-linolenic acid (GLA).

The efficacy of omega-3 and omega-6 fatty acids in the treatment of atopic dermatitis is known. Patent application WO 2015/040067 describes a composition for atopic dermatitis that contains gamma-linolenic fatty acid and eicosapentaenoic fatty acid. R S Mueller et al. describe the efficacy of omega-3 fatty acids in canine atopic dermatitis (*J. Small Anim. Pract.* 45(6), 293-297 (2004)).

Glycosaminoglycans (GAGs) are polymeric biomolecules with a high molecular weight, formed by repetitions of a disaccharide unit. They are found fundamentally in living organisms, where they carry out different physiological functions.

Hyaluronic acid is a non-sulfated glycosaminoglycan, with a polymeric structure characterized by a repeating disaccharide unit, made up of the monosaccharides N-acetyl-D-glucosamine and D-glucuronic acid. It is one of the principal components of cartilage, synovial membrane, and synovial fluid. Specifically, its use is important in the treatment of joint dysfunctions such as osteoarthritis, generally by intra-articular route. Its use has also been described in ophthalmology, healing of wounds, as well as in cosmetics.

Dermatan sulfate is a sulfated glycosaminoglycan with a polymer structure made up mostly of disaccharides of N-acetyl-D-galactosamine sulfated in position 4 and L-iduronic acid, often sulfated in position 2. It has been reported to participate in the wound repair and in the regulation of the coagulation of blood. The U.S. Pat. No. 7,763,594 describes the use of a composition of hyaluronic acid and dermatan sulfate to treat osteoarthritis. Dermatan sulfate should not be confused with chondroitin sulfate. Both polysaccharides are sulfated glycosaminoglycans, but they differ in regard to their origin and structure.

Nucleotides are intracellular compounds with low molecular weight that play a role in practically all biochemical processes. They are present naturally in foods, although in limited quantities (<400 mg/100 g). Tissues with high cellular proliferation rates, such as the ones of the immune system or the intestine are unable to cover their nucleotide requirements solely through de novo synthesis, so they preferably use diet as the method for recuperation of nucleotides. It has been reported that in situations of immune system stress (patients in critical situations), dietary supplementation with nucleotide formulas is vital to maintain the immune system's humoral and cellular response (A. Gil, *European Journal of Clinical Nutrition*, 56 suppl 3, S1-S4 (2002)). Specifically, supplementation with exogenous nucleotides has been demonstrated to stimulate the proliferation of lymphoid cells and the lymphoproliferative response to alloantigens and mitogens. Also, said supplementation contributes to the response of the T lymphocytes, increases the response of delayed cutaneous hypersensitivity, increases the rejection of grafts, reverses the immunosuppression associated with malnutrition, increases resistance to certain infections, regulates the quantity of "natural killer" (NK) cells and macrophages, and promotes synthesis of immunoglobulins (J. Maldonado et al, *Early Human Development*, 65 Suppl., S69-S74 (2001)).

Zinc oxide (ZnO) is used to protect the skin from the harmful effects of ultraviolet rays. Its efficacy in the curing of wounds has also been described (patent EP 1064946).

Hydrolyzed collagen is made up of a mixture of amino acids and peptides with low molecular weight. It is obtained by controlled enzymatic hydrolysis of the collagen protein contained in the skin and in other connective tissues. It is used mostly in cosmetics.

To date no description of the combination of the components of the compositions of the present invention has been found.

DESCRIPTION OF THE INVENTION

Figure 1:
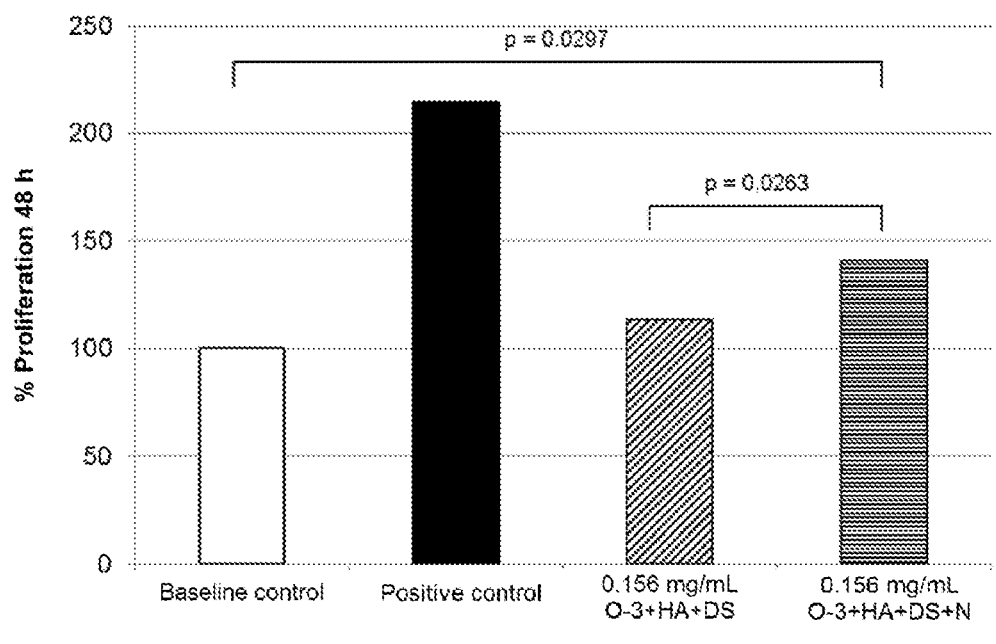
FIG. 1 shows, at the concentration of 0.156 mg/mL, the effect of a composition of the invention containing omega-3 fatty acids, hyaluronic acid, dermatan sulfate, and nucleotides (O-3+HA+DS+N), and the effect of a composition containing omega-3 fatty acids, hyaluronic acid, and dermatan sulfate (O-3+HA+DS) over the percentage of proliferation of human dermal fibroblasts after 48 hours. The Positive Control is also included (culture of human dermal fibroblasts in the presence of TGF-β) and the Baseline Control (culture of human dermal fibroblasts in culture medium and in the absence of the compositions being studied).

The inventors have found that the compositions in the present invention, defined below, are new, present an effect of inducing the proliferation of human dermal fibroblasts, do not present cellular toxicity, and present good healing activity in an in vitro test of wound closure, with a synergistic effect. For this reason, they can be used in the treatment or prevention of a skin disease or lesion selected from the group consisting of atopic dermatitis, allergic dermatitis, demodicosis, psoriasis, wound, ulcer, and burn. They can also be used to restore the integrity of the skin during or after dermatitis or demodicosis, prevent or reverse a psoriatic lesion, increase hydration and flexibility of the skin, prevent the formation of a wound or an ulcer, or improve the quality of healing of a wound, an ulcer, or a burn in a mammal.

Consequently, the present invention relates to a composition comprising hyaluronic acid, dermatan sulfate, at least one omega-3 fatty acid, and at least one nucleotide.

In a preferred embodiment, the omega-3 fatty acid and the hyaluronic acid are present at an omega-3 fatty acid:hyaluronic acid weight ratio comprised between 100:0.50 and 100:5, preferably comprised between 100:0.50 and 100: 2.50. More preferably, the weight ratio is 100:1.13.

In another preferred embodiment, the omega-3 fatty acid and the dermatan sulfate are present at an omega-3 fatty acid:dermatan sulfate weight ratio comprised between 100: 0.10 and 100:2, preferably comprised between 100:0.10 and 100:1. More preferably, the weight ratio is 100:0.23.

In another preferred embodiment, the omega-3 fatty acid and the nucleotide are present at an omega-3 fatty acid: nucleotide weight ratio comprised between 100:20 and 100:200, preferably comprised between 100:20 and 100: 100. More preferably, the weight ratio is 100:52.44.

Preferably, the omega-3 fatty acid, the hyaluronic acid, the dermatan sulfate, and the nucleotide are present at an omega-3 fatty acid:hyaluronic acid:dermatan sulfate:nucleotide weight ratio comprised between 100:0.50:0.10:20 and 100:5:2:200, preferably comprised between 100:0.50:0.10: 20 and 100:2.50:1:100. The weight ratio of 100:1.13:0.23: 52.44 is especially preferred.

In another preferred embodiment, the composition further comprises a zinc compound, preferably, zinc oxide.

In another equally preferred embodiment, the omega-3 fatty acid and the zinc oxide are present at an omega-3 fatty acid:zinc oxide weight ratio comprised between 100:1 and 100:10. Preferably comprised between 100:1 and 100:5. More preferably, the weight ratio is 100:2.42.

Preferably, the omega-3 fatty acid, the hyaluronic acid, the dermatan sulfate, the nucleotide and the zinc oxide are present at an omega-3 fatty acid:hyaluronic acid:dermatan sulfate:nucleotide:zinc oxide weight ratio comprised between 100:0.50:0.10:20:1 and 100:5:2:200:10. Preferably comprised between 100:0.50:0.10:20:1 and 100:2.50:1:100: 5. The weight ratio of 100:1.13:0.23:52.44:2.42 is especially preferred.

In another preferred embodiment, the composition further comprises at least one omega-6 fatty acid.

The omega-3 fatty acid and the omega-6 fatty acid are present at an omega-3 fatty acid:omega-6 fatty acid weight ratio comprised between 1:0.05 and 1:1; the preferable weight ratio is 1:0.13.

Preferably, the omega-3 fatty acid, the hyaluronic acid, the dermatan sulfate, the nucleotide, the zinc oxide and the omega-6 fatty acid are present at an omega-3 fatty acid: hyaluronic acid:dermatan sulfate:nucleotide:zinc oxide: omega-6 fatty acid weight ratio comprised between 100: 0.50:0.10:20:1:5 and 100:5:2:200:10:100. The weight ratio of 100:1.13:0.23:52.44:2.42:13 is especially preferred.

In another preferred embodiment, the omega-3 fatty acid is selected from the group consisting of eicosapentaenoic acid, docosahexaenoic acid, alpha-linolenic acid, stearidonic acid, eicosatetraenoic acid, heneicosapentaenoic acid, docosapentaenoic acid and their mixtures. The most preferred is eicosapentaenoic acid.

In another equally preferred embodiment, the omega-6 fatty acid is selected from the group consisting of gamma-linolenic acid, linoleic acid and their mixtures. The most preferred is gamma-linolenic acid.

Preferably, the eicosapentaenoic acid:gamma-linolenic acid weight ratio is 1:0.075.

Preferably, the concentration of eicosapentaenoic acid is comprised between 50% and 90% by weight, with respect to the total of the omega-3 fatty acids present in the composition. The most preferred concentration is 70%.

Preferably, the concentration of gamma-linolenic acid is between 20% and 60% by weight, with respect to the total weight of the omega-6 fatty acids present in the composition. The most preferred concentration is 40%.

Preferably, the nucleotide is obtained from a yeast, most preferably from *Saccharomyces cerevisiae*.

In another equally preferred embodiment, the composition also comprises hydrolyzed collagen.

Hydrolyzed collagen contains amino acids and peptides with low molecular weight.

In another equally preferred embodiment, the composition also comprises vitamin E.

The present invention also relates to a food supplement, a functional food, or a medical food comprising the composition, defined above, and at least one nutritional additive.

Likewise, the present invention also relates to a pharmaceutical composition that comprises the composition, defined above, and at least one pharmaceutically acceptable excipient.

Likewise, the present invention also relates to a composition, defined above, for use as medicament or medical food.

The present invention also relates to a composition, defined above, for use in the treatment or prevention of a skin disease or lesion selected from the group consisting of atopic dermatitis, allergic dermatitis, demodicosis, psoriasis, wound, ulcer, and burn in a mammal.

Likewise, the present invention also relates to a medical food comprising the composition, defined above, for use in restoring the integrity of the skin during or after dermatitis or demodicosis, preventing or reversing a psoriatic lesion, increasing hydration and flexibility of the skin, preventing the formation of a wound or an ulcer, or improving the quality of healing of a wound, an ulcer, or a burn in a mammal.

Likewise, the present invention also relates to a food supplement, functional food, or medical food comprising the composition, defined above, for use in restoring the integrity of the skin during or after dermatitis or demodicosis, preventing or reversing a psoriatic lesion, increasing hydration and flexibility of the skin, preventing the formation of a wound or an ulcer, or improving the quality of healing of a wound, an ulcer, or a burn in a mammal.

The present invention also relates to the use of a composition, defined above, for the preparation of a medicament for the treatment or prevention of a skin disease or lesion selected from the group consisting of atopic dermatitis, allergic dermatitis, demodicosis, psoriasis, wound, ulcer, and burn in a mammal.

Likewise, the present invention also relates to the use of a composition, defined above, for the preparation of a food supplement, functional food, or medical food, for restoring the integrity of the skin during or after dermatitis or demodicosis, preventing or reversing a psoriatic lesion, increasing hydration and flexibility of the skin, preventing the formation of a wound or an ulcer, or improving the quality of healing of a wound, an ulcer, or a burn in a mammal.

Likewise, the present invention also relates to the use of a composition, defined above, as a food supplement, functional food, or medical food, for restoring the integrity of the skin during or after dermatitis or demodicosis, preventing or reversing a psoriatic lesion, increasing hydration and flexibility of the skin, preventing the formation of a wound or an ulcer, or improving the quality of healing of a wound, an ulcer, or a burn in a mammal.

Preferably, the mammal is a dog or a human.

In the present invention, the term "comprising" must be interpreted such that it also includes the case of "consisting of" and the case of "consisting essentially of".

In the present invention, references to hyaluronic acid and dermatan sulfate include any salts of those substances, for example sodium, potassium, or calcium salt.

Preferably, the form of the hyaluronic acid and the dermatan sulfate of the compositions of the present invention is that of sodium salt.

The omega-3 and omega-6 fatty acids of the compositions of the present invention may be in the form of acids or in the form of triglycerides. Both forms are included, although they are preferably in the form of triglycerides.

In the present invention, the following terms have the specified meanings:

"Functional food" refers to a food that, in addition to its basic nutritional role from the material and energetic point of view, is able to provide a health benefit as a result of containing one or more biologically active components or a combination of biologically active components. Functional food forms part of an individual's diet.

"Food supplement" refers to a diet supplement containing one or more nutrients or other biologically active components in concentrated form, with a beneficial nutritional or physiological effect for health. It is administered in the form of tablets, capsules, or any other dosed form.

"Medical food" refers to a food administered to a patient under the instructions and supervision of a physician. Said food is specifically for the nutritional requirements of a patient who has a particular disease, discomfort, or disorder. It is used in the United States and is normally presented in the form of food, although it may also be found in dosed form. In Europe, the equivalent of "medical food" is "dietetic food for special medical purposes", which is a food intended for a special diet, which has been specially prepared or formulated to satisfy all or some of the dietary needs of patients whose capacity to ingest, digest, absorb, metabolize, or excrete normal foods or specific nutrients of normal foods or metabolites is limited or deficient, or is altered, or who need other clinically determined nutrients, whose dietary treatment cannot be carried out solely by modifying the normal diet, with other foods intended for a special diet, or both. It may or may not be in a dosed form.

The omega-3 and omega-6 fatty acids used in the compositions of the present invention are products that are commercially available. So, for example, to prepare the compositions of the present invention, the omega-3 fatty acids from the company KinOmega (product code: 7010EE) and the omega-6 fatty acids from De Wit Speciality Oils (product code: 41140) may be used.

The hyaluronic acid and the dermatan sulfate of the compositions of the present invention may be obtained through extraction procedures from avian or mammal tissues, or through the use of biotechnology.

The average molecular weights of the hyaluronic acid and the dermatan sulfate of the compositions of the present invention may vary depending on the procedure used to obtain them. Preferably, the average molecular weight of the hyaluronic acid is comprised between 300,000 and 2,000,000 daltons, more preferably between 800,000 and 1,000,000 daltons, and the molecular weight of the dermatan sulfate is comprised between 10,000 and 50,000 daltons. In the present invention, the average molecular weights of the hyaluronic acid and dermatan sulfate were determined by gel permeation chromatography (GPC).

The hyaluronic acid of the compositions of the present invention may be obtained by means of extraction, from avian or mammal tissues, for example from vitreous humor, mammal skin, umbilical cord, or avian combs, or by fermentation of microorganisms (for example *Streptococcus*), following the procedures described in the literature (D. A. Swann, *Biochim. Biophys. Acta* 156, 17-30 (1968); U.S. Pat. No. 4,780,414).

Preferably, the hyaluronic acid of the compositions of the present invention is a commercial product available at www.bioiberica.com. It is obtained from rooster combs, which are chopped and then digested with a proteolytic enzyme. The enzyme is then deactivated by heating and filtered, the dermatan sulfate is eliminated, and the hyaluronic acid is precipitated, anhydrified, dried, and milled. This hyaluronic acid in form of sodium salt presents a minimum richness of 90%, determined by content of glucuronic acid, and an average molecular weight between 800,000 and 1,000,000 daltons.

The dermatan sulfate of the compositions of the present invention may be obtained from avian or mammal tissues, for example from porcine or bovine mucosa, avian combs, or mammal skin following the procedures described in the literature (N. Volpi, *Anal. Biochem.* 218, 382-391 (1994); patent EP 238994).

Preferably, the dermatan sulfate of the compositions of the present invention is obtained from rooster combs, in the procedure to obtain hyaluronic acid. Once the dermatan sulfate has been separated in complex form, the complex is broken by ionic force, precipitated, anhydrified, dried, and milled. The dermatan sulfate from porcine mucosa marketed by the company Sigma-Aldrich Química (product code: C3788) may also be used. This dermatan sulfate in form of sodium salt obtained from rooster combs presents a minimum richness of 90%, determined by photometric titration, and an average molecular weight comprised between 10,000 and 50.000 daltons.

To prepare the compositions of the invention, the product Dermial from Bioibérica, which contains hyaluronic acid and dermatan sulfate, can be used.

Examples of the nucleotides in the compositions of the present invention are adenosine 5'-monophosphate (AMP), guanosine 5'-monophosphate (GMP), uridine 5'-monophosphate (UMP), cytidine 5'-monophosphate (CMP), deoxythymidine 5'-monophosphate (dTMP), deoxycytidine 5'-monophosphate (dCMP), inosine 5'-monophosphate (IMP), as well as the corresponding diphosphates and triphosphates.

Preferably, the nucleotides of the present invention are obtained from a yeast, more specifically the yeast *Saccharomyces cerevisiae*. Specifically, they are obtained from the RNA of the yeast *Saccharomyces cerevisiae*. They can also be obtained from the RNA of the yeast *Torula utilis*. The method for obtaining the nucleotides consists of extracting the RNA from the yeast, followed by the purification and hydrolysis of the RNA. The products Nucleoforce®, Nucleoforce® Dogs, Nucleoforce® Piglets or Nucleoforce® Poultry®, which are marketed by the company Bioiberica S.A. (www.bioiberica.com), and which can be used in the present invention as a source of nucleotides, are obtained from the RNA of the yeast *Saccharomyces cerevisiae*. Other nucleotides available on the market may also be used, for example Ascogen®, Vannagen®, Ascosan®, Bioracing® from Chemoforma (www.chemoforma.com), or Provesta® from Ohly (www.ohly.com), or Nupro from Alltech (www.alltech.com).

Zinc oxide is a commercial product. The zinc oxide marketed by Kirsch Pharma España (product code: 101217) can be used in the compositions of the present invention.

The hydrolyzed collagen of the compositions of the present invention can be obtained from mammal skin or rooster crests, following the procedures described in the literature ("Final Report on the Safety Assessment of Hydrolyzed Collagen", *Journal of the American College of Toxicology* 4, no 5, 199-221, Mary Ann Liebert, Inc., Publishers, (1985)).

The compositions of the present invention can be prepared by mixing their individual components in the desired proportions.

Several components of the compositions of the present invention can be obtained together. This means that the hyaluronic acid, dermatan sulfate and hydrolyzed collagen combination can be obtained from avian or mammal tissues using an extraction procedure. For example, the process may begin with frozen rooster combs, which are chopped and then digested with a proteolytic enzyme. The enzyme is then deactivated by heating, followed by filtering and precipitation with solvents. The hyaluronic acid and dermatan sulfate combination can be obtained by slightly modifying this method.

The most preferable composition of the invention is the composition that comprises 57.97% of omega-3 fatty acids (O-3), 0.66% hyaluronic acid (HA), 0.15% dermatan sulfate (DS), 30.40% nucleotides (N), 1.40% zinc oxide (ZnO) and 7.60% omega-6 fatty acids (O-6) (weight ratio O-3:HA:DS:N:ZnO:O-6 100:1.13:0.23:52.44:2.42:13).

The composition may also contain 1.82% vitamin E.

To use the compositions of the present invention in the treatment, prophylaxis, or prevention of atopic dermatitis, allergic dermatitis, demodicosis, psoriasis, wounds, ulcers, or burns in mammals, they are formulated into suitable pharmaceutical compositions, using conventional techniques and excipients or vehicles, such as those described in *Remington: The Science and Practice of Pharmacy* 2000, edited by Lippincott Williams and Wilkins, 20th edition, Philadelphia. The pharmaceutical compositions comprise a therapeutically effective quantity of a composition of the present invention and at least one pharmaceutically acceptable excipient for administration to the patient. Said pharmaceutical compositions can be administered to the patient in required doses. Pharmaceutical compositions may be administered using different routes, for example, oral, intravenous, subcutaneous, intramuscular, sublingual, intradermal, nasal, or topical. The pharmaceutical compositions of the invention include a therapeutically effective quantity of a composition of the present invention, with said quantity depending on many factors, such as the physical condition of the patient, age, sex, route of administration, frequency of administration, or severity of the disease. It will also be understood that said dosage of the composition of the invention may be administered in single or multiple dose units to provide the desired therapeutic effects.

The pharmaceutical compositions of the invention will generally be in solid, liquid, or gel form. The pharmaceutical preparations in solid form that can be prepared in accordance with the present invention include powders, minigranules (pellets), tablets, dispersible granules, capsules, cachets, pills, lyophilisates, and suppositories. The preparations in liquid form include solutions, suspensions, emulsions, syrups, elixirs, drinkable vials, and infusions. The preparations in solid form that are to be converted into liquid preparations immediately prior to use are also included. These liquid forms include solutions, suspensions, and emulsions.

To use the compositions of the present invention in restoring the integrity of the skin during or after dermatitis or demodicosis, preventing or reversing a psoriatic lesion, increasing the hydration and flexibility of the skin, preventing the formation of a wound or ulcer, or improving the quality of healing of wounds, ulcers, or burns in mammals, food supplements or dietetic foods for special medical purposes are prepared in dosed forms containing a composition of the invention and additives used in nutrition, or functional foods are prepared, adding the compositions of the invention to the foods that form part of the diet, or medical foods or dietetic foods for special medical purposes are prepared in non-dosed forms containing a composition of the invention and nutrients or foods. The food supplement may be in the form of tablets, capsules, solutions, suspensions, or sachets. The functional food may be in the form of yogurt, milk, fermented milk, fruit juices, vegetable juices, soups, purees, dehydrated foods, cookies or baby food. The dietetic food for special medical purposes may be in the form of tablets, capsules, solutions, suspensions, or sachets, or also as a food for special patient diets. The medical food is normally presented in the form of food for patient diets, although it may also be found in dosed forms.

The pharmaceutical compositions, food supplements, functional foods, or medical foods of the present invention may also contain at least one vitamin, selected from the group consisting of vitamin C, vitamin E, vitamin A, folic acid, niacin, pantothenic acid, vitamin B2, vitamin B6, vitamin B12, vitamin D and biotin.

DETAILED DESCRIPTION OF THE PREFERRED EMBODIMENTS

The following examples are provided for the purposes of illustration and do not represent any limitation of the scope of the present invention.

Example 1: Soft Gelatin Capsules

The capsules were prepared following conventional procedures.

Each capsule contained:

| | |
|---|---|
| omega-3 fatty acids | 572.00 mg |
| hyaluronic acid* | 6.50 mg |
| dermatan sulfate* | 1.34 mg |
| nucleotides | 300.00 mg |
| zinc oxide | 13.88 mg |
| omega-6 fatty acids | 75.00 mg |

*The hyaluronic acid and dermatan sulfate may be substituted by 10 mg of Dermial, which contains hyaluronic acid and dermatan sulfate.

Example 2: Soft Gelatin Capsules with Vitamin E

The capsules were prepared following conventional procedures.

Each capsule contained:

| | |
|---|---|
| omega-3 fatty acids | 572.00 mg |
| hyaluronic acid* | 6.50 mg |
| dermatan sulfate* | 1.34 mg |
| nucleotides | 300.00 mg |
| zinc oxide | 13.88 mg |
| omega-6 fatty acids | 75.00 mg |
| vitamin E | 18.00 mg |

*The hyaluronic acid and dermatan sulfate may be substituted by 10 mg of Dermial, which contains hyaluronic acid and dermatan sulfate.

Example 3: Stimulation Activity of the Proliferation of Fibroblasts of a Composition of the Invention Containing Omega-3 Fatty Acids, Hyaluronic Acid, Dermatan Sulfate, and Nucleotides. Comparison with a Composition that does not Contain Nucleotides Fibroblasts, along with keratinocytes, are the principal cells in the dermis and epidermis. Their migration and proliferation are involved in the process of re-epithelialization, which is very necessary in skin pathologies in which the dermal barrier is altered and patients present lesions caused by the pathology itself or by scratching due to itching. The aim of this study was to determine the stimulation activity of the proliferation of human dermal fibroblasts of a composition of the invention that contained omega-3 fatty acids, hyaluronic acid, dermatan sulfate, and nucleotides, comparing it with a composition that contained omega-3 fatty acids, hyaluronic acid, and dermatan sulfate. The two compositions were compared at the same final concentration of 0.156 mg/mL.

A composition of the invention that contained 65.38% of omega-3 fatty acids (O-3), 0.64% hyaluronic acid (HA), 0.15% dermatan sulfate (DS), and 34.13% nucleotides (N) (weight ratio O-3:HA:DS:N 100:0.98:0.23:52.20) was used.

The three-component composition contained 98.65% of omega-3 fatty acids (O-3), 1.12% hyaluronic acid (HA) and 0.23% dermatan sulfate (DS) (weight ratio O-3:HA:DS 100:1.13:0.23).

Materials and Methods

The degree of proliferation was quantified by measuring the incorporation of bromodeoxyuridine (BrdU) during DNA synthesis in fibroblasts in proliferation.

The human dermal fibroblasts were seeded at 5,500 cells/well in dishes with 96 wells, and after 6-7 hours, they were left with a growth-factor deprived culture medium overnight. The next day, the cells were treated with a composition of the present invention, at a concentration of 0.156 mg/mL, that contained omega-3 fatty acids, hyaluronic acid, dermatan sulfate, and nucleotides (O-3+HA+DS+N), or with a composition at a concentration of 0.156 mg/mL that contained omega-3 fatty acids, hyaluronic acid, and dermatan sulfate (O-3+HA+DS). The quantity of absorbance was determined by spectrophotometry after 48 hours of exposure of the culture to the compositions being studied.

As Baseline Control, the cells were not treated; and as Positive Control, the fibroblasts were exposed to TGF-β1 (25 ng/mL).

Results

As shown in FIG. 1, the composition of the present invention (O-3+HA+DS+N) at the dosage of 0.156 mg/mL and after 48 hours, showed a statistically significant stimulating effect (p=0.0297) of the proliferation of fibroblasts, if compared with the Baseline Control. Specifically, proliferation increased by 40.70%. However, at the same dosage of 0.156 mg/mL, the composition that contained omega-3 fatty acids, hyaluronic acid, and dermatan sulfate (O-3+HA+DS), but did not contain nucleotides did not show efficacy (a tendency to stimulate fibroblast proliferation was observed, but it was not statistically significant when compared with the Baseline Control). FIG. 1 also shows the statistically significant difference (p=0.0263) between the two compositions.

Example 4: Stimulation Activity of the Proliferation of Fibroblasts of a Composition of the Invention Containing Omega-3 Fatty Acids, Hyaluronic Acid, Dermatan Sulfate, Nucleotides, and ZnO. Comparison with a Composition that does not Contain Nucleotides or ZnO The aim of this study was to determine the stimulation activity of the proliferation of human dermal fibroblasts of a composition of the present invention that contained omega-3 fatty acids, hyaluronic acid, dermatan sulfate, nucleotides, and ZnO, comparing it with a composition that contained omega-3 fatty acids, hyaluronic acid, and dermatan sulfate. The two compositions were compared at the same final concentration of 0.078 mg/mL.

A composition of the invention that contained 64.10% of omega-3 fatty acids (O-3), 0.76% hyaluronic acid (HA), 0.12% dermatan sulfate (DS), 33.33% nucleotides (N) and 1.28% of ZnO (weight ratio O-3:HA:DS:N:ZnO 100:1.20:0.20:52:2) was used.

The composition of three components contained 98.65% of omega-3 fatty acids (O-3), 1.12% hyaluronic acid (HA) and 0.23% dermatan sulfate (DS) (weight ratio O-3:HA:DS 100:1.13:0.23).

Materials and Methods

The same methodology used in Example 3 was applied, but in this case, the culture was exposed for 24 hours to the compositions being studied, which were prepared with a final concentration of 0.078 mg/mL.

Results

Figure 2:
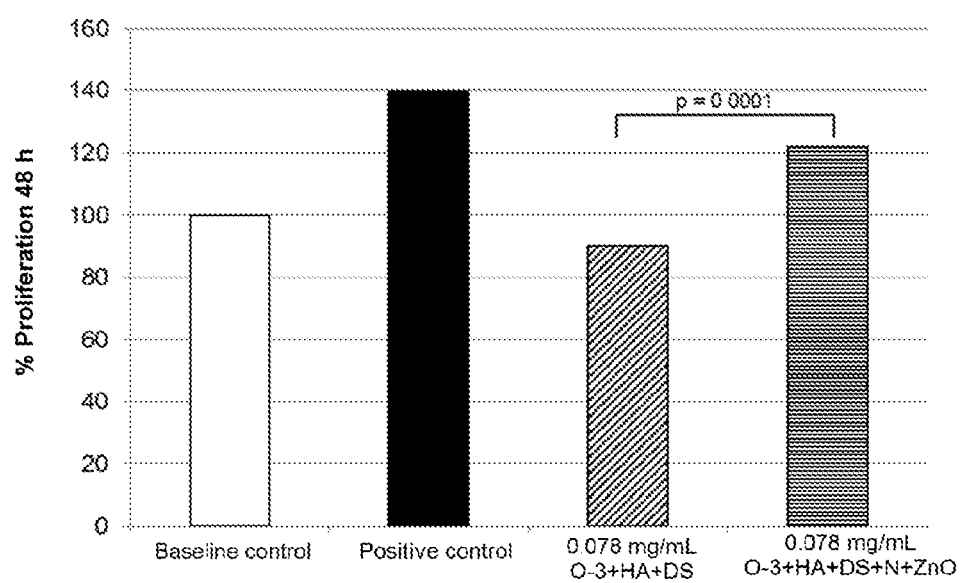
FIG. 2 shows, at the concentration of 0.078 mg/mL, the effect of a composition of the invention containing omega-3 fatty acids, hyaluronic acid, dermatan sulfate, nucleotides, and zinc oxide (O-3+HA+DS+N+ZnO), and the effect of a composition containing omega-3 fatty acids, hyaluronic acid, and dermatan sulfate (O-3+HA+DS) over the percentage of proliferation of human dermal fibroblasts after 24 hours. The Positive Control is also included (culture of human dermal fibroblasts in the presence of TGF-β) and the Baseline Control (culture of human dermal fibroblasts in culture medium and in the absence of the compositions being studied).

As shown in FIG. 2, at the dose of 0.078 mg/mL and after 24 hours, there was a statistically significant difference ($p=0.0001$) between the composition of the present invention ((O-3+HA+DS+N+ZnO) and the composition that contained omega-3 fatty acids, hyaluronic acid, and dermatan sulfate (O-3+HA+DS), but that did not contain nucleotides or zinc oxide.

Example 5: Study of the Healing Activity and Synergy of a Composition of the Invention Containing Omega-3 Fatty Acids, Hyaluronic Acid, Dermatan Sulfate, Nucleotides, and ZnO One aim of this study was to determine the healing activity of a composition of the invention with five components, comparing it with a composition that contained only three components (omega-3 fatty acids, hyaluronic acid, and dermatan sulfate) through an in vitro trial on wound closure. Another aim was to determine whether the composition of the invention with five components (omega-3 fatty acids, hyaluronic acid, dermatan sulfate, nucleotides, and zinc oxide) was synergistic.

Materials and Methods

Human dermal fibroblasts (HDF) were used, which were cultivated in dishes with 24 wells with a surface area of 1.99 $cm^2$, with a density of $7 \times 10^4$ cells/well. A mark was made in a straight line approximately 2 mm wide on the surface of the single layer of cells using a sterile plastic tip, creating an area free of cells. Immediately afterward, the compounds or compositions were applied to the cultures in the following concentrations:

Omega-3 fatty acids (O-3): 0.156 mg/mL
Hyaluronic acid (HA): 0.0017 mg/mL
Dermatan sulfate (DS): 0.0004 mg/mL
Nucleotides (N): 0.0818 mg/mL
Zinc oxide (ZnO): 0.0027 mg/mL Three-component composition: 0.156 mg/mL O-3+0.0017 mg/mL HA+0.0004 mg/mL DS (weight ratio O-3:HA:DS 100:1.09:0.25)

Four-component composition of the invention: 0.156 mg/mL O-3+0.0017 mg/mL HA+0.0004 mg/mL DS+0.0818 mg/mL N (weight ratio O-3:HA:DS:N 100:1.09:0.25:52.43)

Five-component composition of the invention: 0.156 mg/mL O-3+0.0017 mg/mL HA+0.0004 mg/mL DS+0.0818 mg/mL N+0.0027 mg/mL ZnO (weight ratio O-3:HA:DS:N:ZnO 100:1.09:0.25:52.43:1.73)

The untreated cells were used as the negative control. The positive control was the Dulbeco's medium (DMEM) culture supplemented with fetal bovine serum (FBS) at 0.1%.

The cells were then allowed to migrate to the center of the dish, to cover the area free of cells, in the presence of the compounds being studied, and the area covered with cells was quantified after 48 hours using the TIRF Automated Inverted Microscope—ScanR Olympus (Leica) and a 4× objective lens (total amplification 40×). Each experimental condition was carried out in triplicate.

To determine the healing activity of each treatment, the area covered by cells was quantified, in $\mu m^2$, before (T0 h) and after (48 h) the treatment, using image analysis using the software Image J. The results were compared with those obtained for the negative and positive controls.

Results

Figure 3:
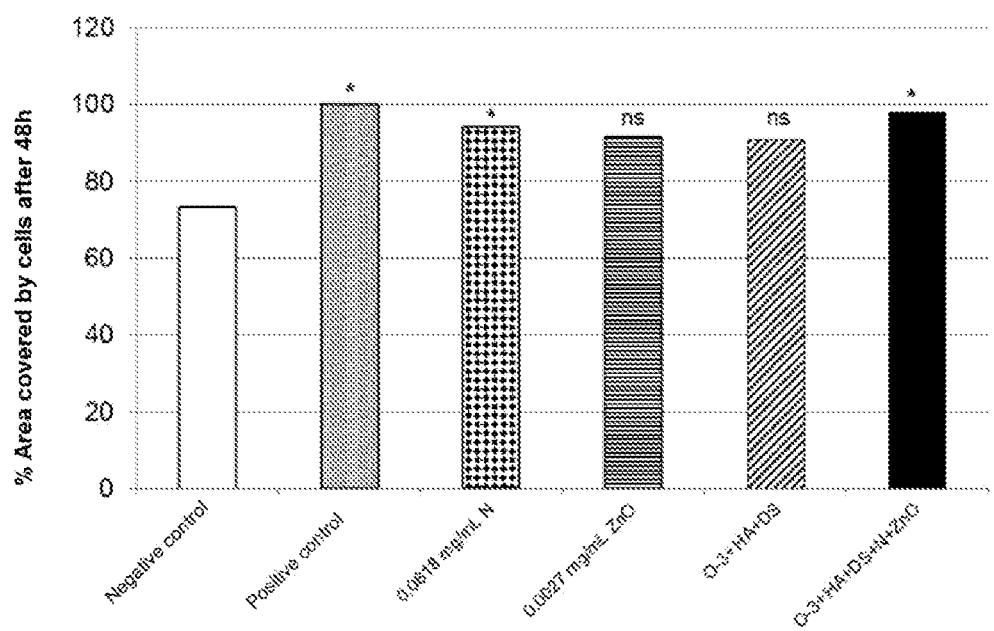
FIG. 3 shows the % of the area covered with cells, 48 hours after applying 0.0818 mg/mL of nucleotides (N), 0.0027 mg/mL of ZnO, O-3+HA+DS (0.156 mg/mL O-3+ 0.0017 mg/mL HA+0.0004 mg/mL DS) or O-3+HA+DS+ N+ZnO (0.156 mg/mL O-3+0.0017 mg/mL HA+0.0004 mg/mL DS+0.0818 mg/mL N+0.0027 mg/mL ZnO) to the wound. The negative control refers to untreated cells.

FIG. 3 shows that the composition of the invention O-3+HA+DS+N+ZnO is synergistic. The combination of nucleotides, ZnO and the three-component composition (O-3+HA+DS) presented a synergistic healing effect, exceeding the sum of the individual components separately.

Figure 4:
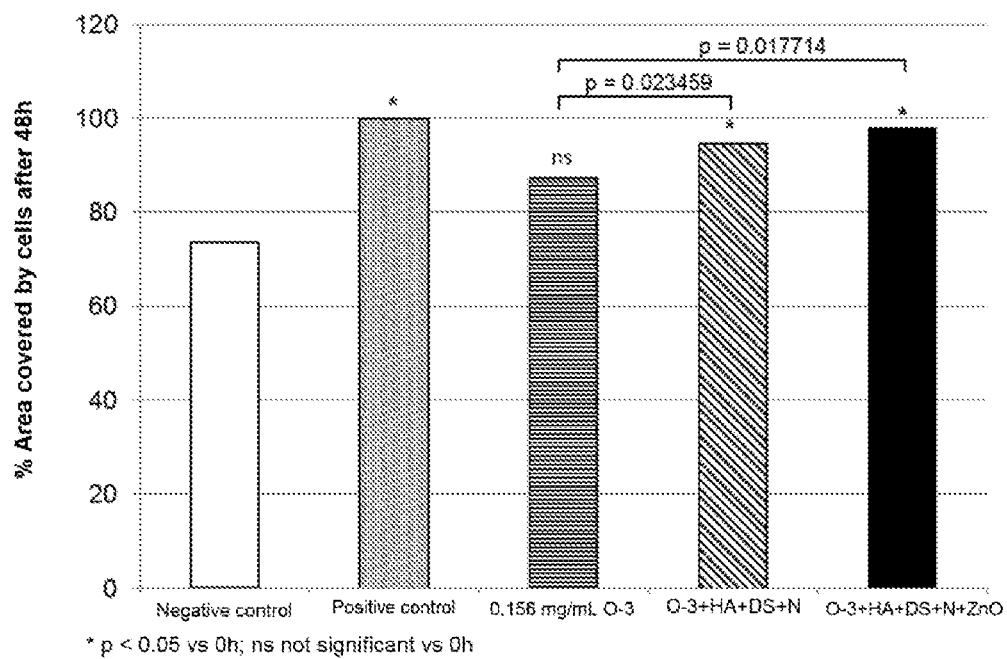
FIG. 4 shows the % of the area covered with cells, 48 hours after applying 0.156 mg/mL of O-3, O-3+HA+DS+N (0.156 mg/mL O-3+0.0017 mg/mL HA+0.0004 mg/mL DS+0.0818 mg/mL N) or O-3+HA+DS+N+ZnO (0.156 mg/mL O-3+0.0017 mg/mL HA+0.0004 mg/mL SD+0.0818 mg/mL N+0.0027 mg/mL ZnO) to the wound. The two compositions of the invention with the omega-3 fatty acids (O-3) are compared. The negative control refers to untreated cells.

FIG. 4 shows that the omega-3 fatty acids did not cause a significant increase in healing, but a significant increase in healing ($p<0.05$) was observed when HA+DS+N was added to obtain the four-component composition of the invention (O-3+HA+DS+N) and when HA+DS+N+ZnO was added to the omega-3 fatty acids to obtain the five-component composition of the invention (O-3+HA+DS+N+ZnO). Also, when the increase in healing was compared between groups, a significant difference was found between the four-component invention and the O-3 ($p=0.023459$), and between the five-component invention (O-3+HA+DS+N+ZnO) and the O-3 ($p=0.017714$).

Figure 5:
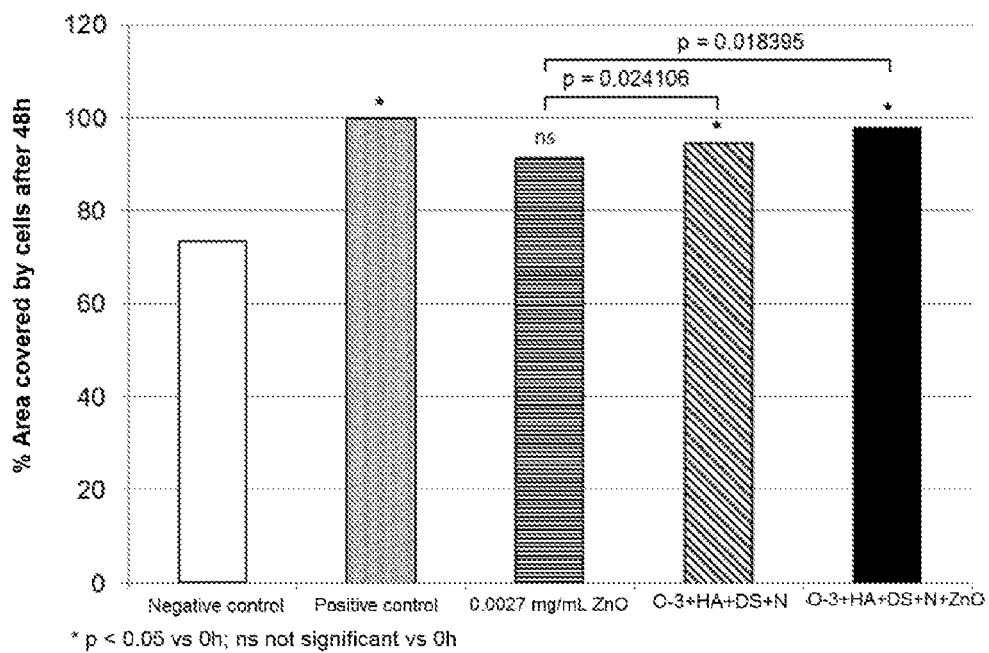
FIG. 5 shows the % of the area covered with cells, 48 hours after applying 0.0027 mg/mL of ZnO, O-3+HA+ DS+N (0.156 mg/mL O-3+0.0017 mg/mL HA+0.0004 mg/mL DS+0.0818 mg/mL N) or O-3+HA+DS+N+ZnO (0.156 mg/mL O-3+0.0017 mg/mL HA+0.0004 mg/mL DS+0.0818 mg/mL N+0.0027 mg/mL ZnO) to the wound. The two compositions of the invention with ZnO are compared. The negative control refers to untreated cells.

Also, FIG. 5 shows that the ZnO did not cause a significant increase in healing and that the four-component compositions of the invention (O-3+HA+DS+N) and five-component compositions of the invention (O-3+HA+DS+N+ZnO) presented a significant difference with respect to the ZnO ($p=0.024106$ and $p=0.018395$, respectively).

The invention claimed is:

1. A composition comprising:
hyaluronic acid,
dermatan sulfate,
an omega-3 fatty acid selected from the group consisting of: eicosapentaenoic acid, docosahexaenoic acid, alpha-linolenic acid, stearidonic acid, eicosatetraenoic acid, heneicosapentaenoic acid, docosapentaenoic acid, and mixtures thereof, and
a yeast RNA nucleotide selected from the group consisting of cytidine 5'-monophosphate (CMP), uridine 5'-monophosphate (UMP), adenosine 5'-monophosphate (AMP), guanosine 5'-monophosphate (GMP), inosine 5'-monophosphate (IMP), and mixtures thereof.

2. The composition according to claim 1, wherein a weight ratio of the omega-3 fatty acid to the hyaluronic acid is between 100:0.50 and 100:5.

3. The composition according to claim 1, wherein a weight ratio of the omega-3 fatty acid to the dermatan sulfate is between 100:0.10 and 100:2.

4. The composition according to claim 1, wherein a weight ratio of the omega-3 fatty acid to the yeast RNA nucleotide is between 100:20 and 100:200.

5. The composition according to claim 1, further comprising a zinc compound, wherein the zinc compound is zinc oxide.

6. The composition according to claim 5, wherein a weight ratio of the omega-3 fatty acid to the zinc oxide is between 100:1 and 100:10.

7. The composition according to claim 5, wherein a weight ratio of the omega-3 fatty acid to the hyaluronic acid to the dermatan sulfate to the yeast RNA nucleotide to the zinc oxide is between 100:0.50:0.10:20:1 and 100:5:2:200:10.

8. The composition according to claim 5, further comprising an omega-6 fatty acid selected from the group consisting of gamma-linolenic acid, linoleic acid and mixtures thereof.

9. The composition according to claim 1, further comprising an omega-6 fatty acid selected from the group consisting of gamma-linolenic acid, linoleic acid and mixtures thereof.

10. A food supplement, functional food, or medical food comprising the composition defined in claim 1.

11. A pharmaceutical composition comprising the composition defined in claim 1, and at least one pharmaceutically acceptable excipient.

12. A method of treating a skin disease or lesion comprising administering the composition according to claim 1 to a subject in need thereof, wherein the skin disease or lesion is selected from the group consisting of atopic dermatitis, allergic dermatitis, and psoriasis.

13. The method according to claim 12, wherein the treating a skin disease or lesion comprises at least one of restoring integrity of skin during or after dermatitis or demodicosis, reversing a psoriatic lesion, increasing hydration and flexibility of skin, and improving the quality of healing of a wound, an ulcer, or a burn.

14. The method according to claim 12, wherein the composition further comprises zinc oxide.

15. The method according to claim 12, wherein the composition further comprises zinc oxide and a weight ratio of the omega-3 fatty acid to the hyaluronic acid to the dermatan sulfate to the yeast RNA nucleotide to the zinc oxide is between 100:0.50:0.10:20:1 and 100:5:2:200:10.

16. The method according to claim 12, wherein the composition further comprises zinc oxide and an omega-6 fatty acid selected from the group consisting of gamma-linolenic acid, linoleic acid and mixtures thereof.

* * * * *